United States Patent [19]

Otagawa et al.

[11] Patent Number: 4,900,405

[45] Date of Patent: Feb. 13, 1990

[54] SURFACE TYPE MICROELECTRONIC GAS AND VAPOR SENSOR

[75] Inventors: Takaaki Otagawa, Fremont; Marc J. Madou, Palo Alto, both of Calif.

[73] Assignee: SRI International, Menlo Park, Calif.

[21] Appl. No.: 73,712

[22] Filed: Jul. 15, 1987

[51] Int. Cl.$^4$ ............................................. G01N 27/26
[52] U.S. Cl. ..................................... 204/1 T; 204/412; 204/280
[58] Field of Search ............... 204/1 T, 412, 415, 421, 204/424, 426, 430, 280

[56] References Cited

U.S. PATENT DOCUMENTS

| | | | |
|---|---|---|---|
| 3,247,452 | 4/1966 | Kordesch . | |
| 3,464,008 | 8/1969 | Meysson et al. . | |
| 3,703,696 | 11/1972 | Browall et al. . | |
| 3,820,402 | 6/1974 | Interrante et al. . | |
| 3,891,958 | 6/1975 | Wakabayashi . | |
| 4,016,308 | 4/1977 | Frazee . | |
| 4,076,596 | 2/1978 | Connery et al. . | |
| 4,140,990 | 2/1979 | Warrens . | |
| 4,227,984 | 10/1980 | Dempsey et al. | 204/430 |
| 4,228,400 | 10/1980 | Bruckenstein et al. . | |
| 4,277,323 | 7/1981 | Muller et al. | 204/426 |
| 4,441,073 | 4/1984 | Davis . | |
| 4,492,622 | 1/1985 | Kuypers | 204/415 |
| 4,510,436 | 4/1985 | Raymond . | |
| 4,536,274 | 8/1985 | Papadakis et al. | 204/415 |
| 4,571,292 | 2/1986 | Liu et al. | 204/412 |
| 4,571,543 | 2/1986 | Raymond et al. . | |
| 4,593,304 | 6/1986 | Slayman . | |
| 4,636,767 | 1/1987 | Barger et al. . | |
| 4,638,286 | 1/1977 | Nichols . | |
| 4,668,374 | 5/1987 | Bhagat et al. | 204/426 |

FOREIGN PATENT DOCUMENTS 150748 9/1981 Japan .

OTHER PUBLICATIONS

Koudelka, Performance Characteristics of a Planar "Clark-Type" Oxygen Sensor, 9, (1986), 249-258.
Koudelka et al., Miniaturized "Clark-Type" Oxygen Sensor, Centre Suisse d'Electronique et de, Microtechnique S.A., Neuchatel, Switzerland, CH2127-9/85/00-00-0418, 1985, IEEE.

*Primary Examiner*—Donald L. Walton
*Attorney, Agent, or Firm*—Fliesler, Dubb, Meyer & Lovejoy

[57] ABSTRACT

The present invention is concerned with electrode structures and microsensors having fast response times and high sensitivity and to methods using such structures and/or microsensors. This is accomplished in any one of several ways. In one, the sensing and counter electrodes are positioned close enough together on an active area so that ion migration therebetween is fast. The thickness of the electrolytic medium on the active area is restricted to be no more than about 10 microns so that diffusion therethrough between the electrodes is at least as fast as the ion migration. In another, the sensing electrode may have outwardly extending portions extending beyond the electrolytic medium and not being covered thereby. Or, conductive particles can be distributed in the electrolytic medium. Or the medium can be very thin. Or, the electrodes can be interdigited. Combinations of the above structural features are also set forth.

88 Claims, 8 Drawing Sheets

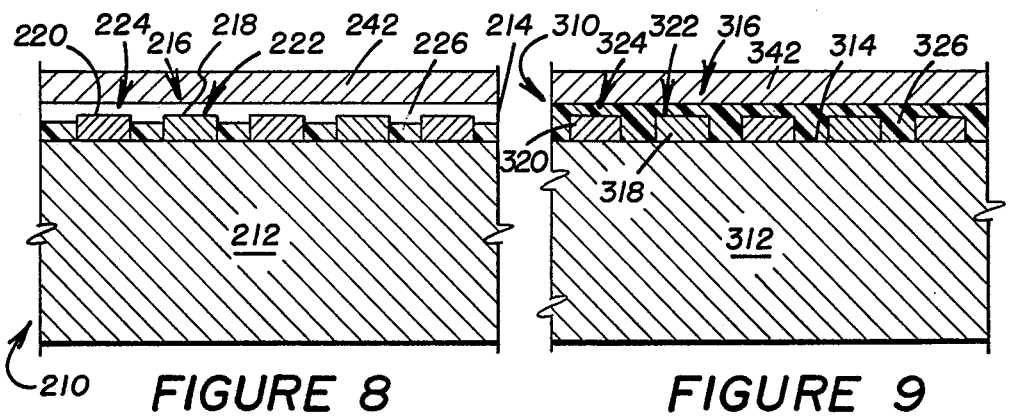
FIGURE 8    FIGURE 9
FIGURE 10
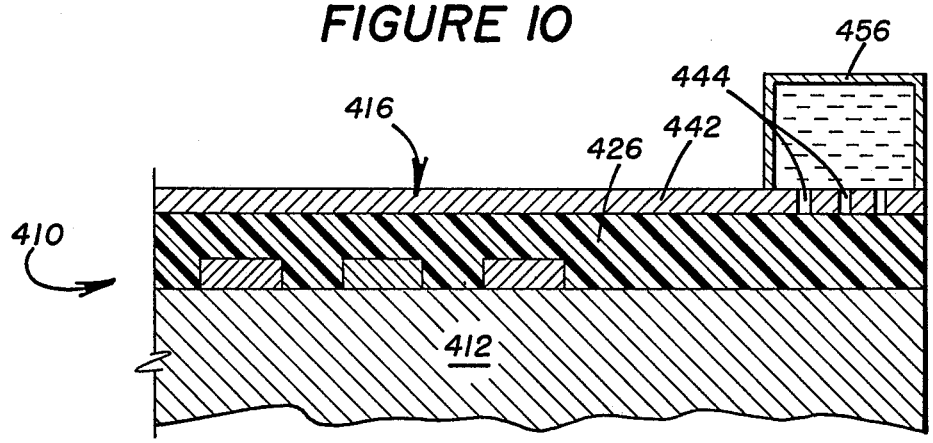
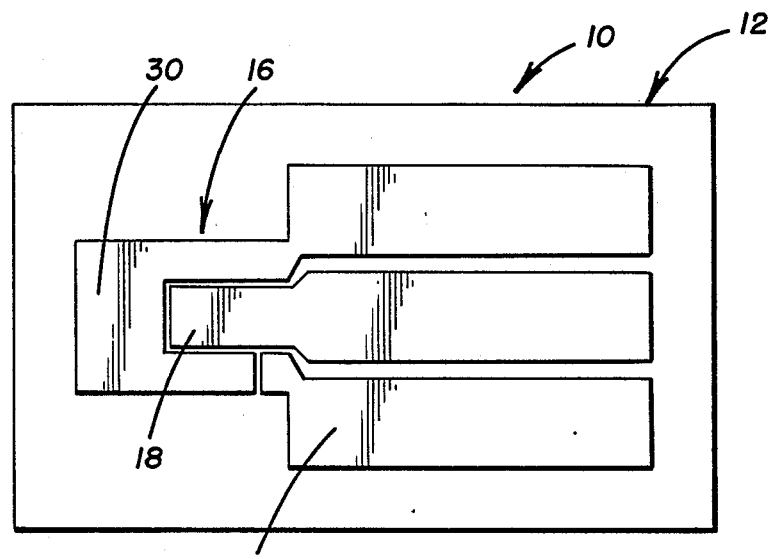
FIGURE 11

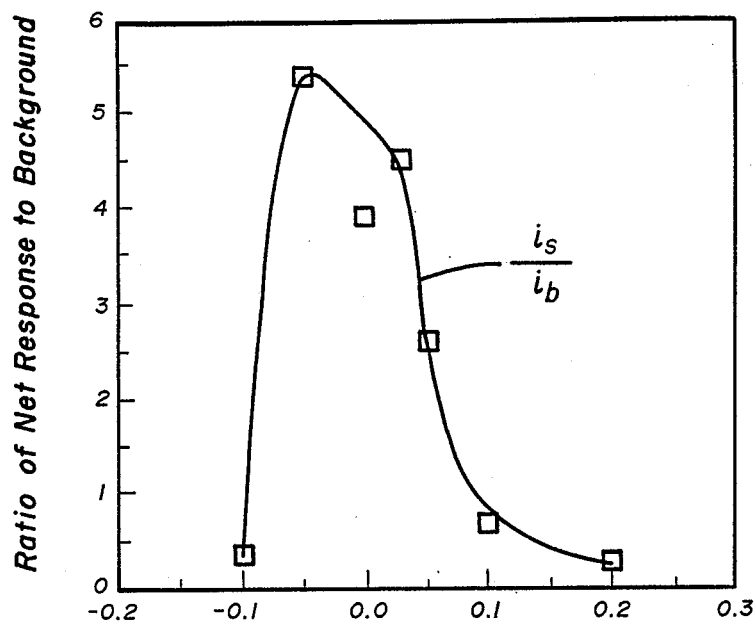
FIGURE 15   Applied Potential vs Reference
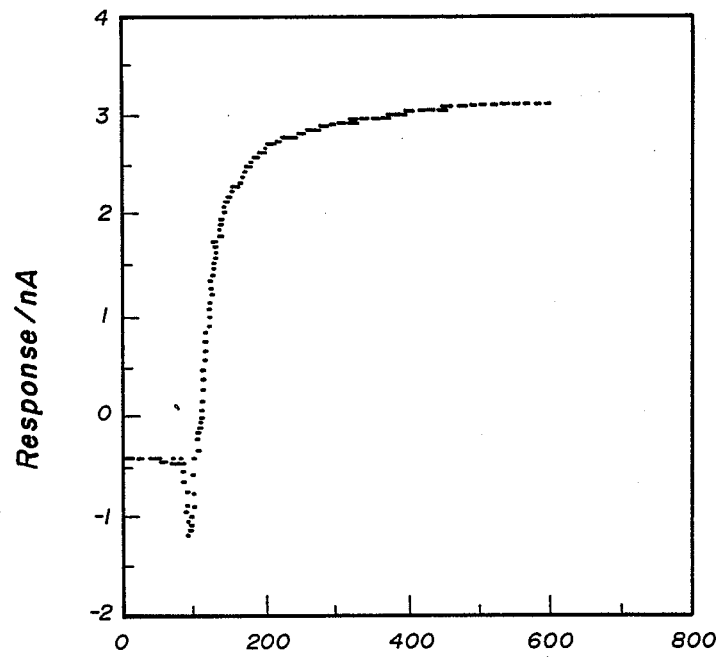
FIGURE 16   TIME (Sec)

SURFACE TYPE MICROELECTRONIC GAS AND VAPOR SENSOR

TECHNICAL FIELD

The present invention relates to a surface conforming microsensor structure which is capable of analyzing a gas and/or vapor mixture for one or more specific components thereof, or for one or more gases and/or vapors dissolved in a liquid, and to analysis methods using such a sensor.

BACKGROUND ART

A number of gas sensors are known to the art. For example, U.S. Pat. No. 4,227,984, issued to Dempsey, et al, discloses a potentiostated 3; -electrode solid polymer electrolyte (SPE) gas sensor. The sensor structure disclosed in this patent has catalytic sensing and counter electrodes on opposite sides of a solid polymeric electrolyte membrane. Miniaturization of such a structure is extremely difficult. Long term stability of the electrode-SPE interface is quite poor due to the swelling nature of the SPE. Still further, such a sensor is not readily adapted to the formation of arrays which can measure a number of different gaseous species or which can provide redundancy in the measurement of one or more gaseous species. Further yet, the construction of such sensors is relatively expensive.

Surface conforming substantially planar sensors are also known to the art. For example, M. Koudelka describes a planar "Clark-type" oxygen sensor in "Sensors and Actuators", 9 (1986) 249–258. Also, M. Koudelka and A. Grisel, describe such a planar sensor in "Miniaturized" "Clark-type" "Oxygen Sensor" as reported in Proceedings of Transducers 85 (Philadelphia, Pa., June 1985). The sensor or sensors described by Koudelka and by Koudelka and Grisel are in the nature of planar 2-electrode oxygen sensors fabricated using standard integrated circuit (IC) technology. The sensors consist of a silver cathode and a silver/silver chloride/chloride ion reference anode. The electrodes are in a planar orientation upon a silicon dioxide layer upon a silicon substrate. An electrolytic medium, in the nature of a hydrogel layer, completely covers the electrodes and their surfaces to a substantial depth, generally at least about 40 to 50 microns. A silicon rubber membrane, generally 25 to 50 microns thick, having pores which are porous to oxygen encapsulates the hydrogel layer and the electrodes. While the planar sensor just described has a number of advantages it is not as sensitive as would be desired and does not have as fast a response time as would be desired since the analyte gas must pass through the hydrogel layer to reach the sensing electrode.

The present invention is directed to overcoming one or more of the problems as set forth above.

DISCLOSURE OF INVENTION

In accordance with another embodiment of the invention an improved microsensor structure is set forth. The microsensor structure comprises a substrate having a sensing electrode, a counter electrode and a reference electrode all mounted on an active area on the surface of the substrate, the electrodes defining sensing-counter, sensing-reference and counter-reference gaps, the gaps being bridged by a solid polymer electrolyte.

In accordance with an embodiment of the present invention a method is set forth of determining the concentration of a gaseous species. The method comprises contacting a microsensor structure with a gaseous species in a gas phase and measuring the electrochemical effect of the species between sensing and counter electrodes. The microsensor structure comprises a substrate having a sensing electrode, a counter electrode and a reference electrode all mounted on an active area on the surface of the substrate, the electrodes defining sensing-counter, sensing-reference and counter-reference gaps, the gaps being bridged by a solid polymer electrolyte.

In accordance with a different embodiment of the present invention an improved structure is set forth for determining a gaseous species. The structure comprises a substrate surface having an active area. First and second adjacent electrodes have, respectively, sensing and counter portions on the active area. A solid electrolytic medium covers the active area. The improvement in the structure includes positioning the first and second electrodes sufficiently close together so that the time of migration of an ionic moiety from one to the other of the electrodes is no more than about 1 minute; and restricting the thickness of the electrolytic medium to be no more than about 10 microns so that the time of diffusion of the gaseous species through the electrolytic medium to the first electrode is no more than about equal to the time of migration of the ionic moiety from one to the other of the first and second electrodes.

In accordance with still a different embodiment of the invention a method is set forth of determining the concentration of a gaseous species. The method comprises contacting a microsensor structure with the gaseous species in a gas phase and measuring the electrochemical effect of the species between the first and second electrodes. The microsensor structure comprises a substrate surface having an active area. First and second adjacent electrodes have, respectively, sensing and counter portions on the active area. A solid electrolytic medium covers the active area. The first and second electrodes are positioned sufficiently close together so that the time of migration of an ionic moiety from one to the other of the electrodes is no more than about 1 minute. The thickness of the electrolytic medium is no more than about 10 microns so that the time of diffusion of the gaseous species through the electrolytic medium is no more than about equal to the time of migration of the ionic moiety from one to the other of the electrodes.

A microsensor structure is still an additional embodiment of the invention. The microsensor structure comprises a substrate having a surface having an active area. A sensing electrode has a sensing portion on the active area, the sensing portion comprising a plurality of sensing fingers. A counter electrode has a counter portion on the active area. The counter portion comprises a plurality of counter fingers. The counter fingers are positioned between and aligned along the sensing fingers to define sensing finger-counter finger gaps of no more than about 50 microns. A reference electrode has a reference portion on said active area. An electrolytic medium is on the active area, bridges the sensing finger-counter finger gaps and communicates the reference portion with said sensing portion.

Yet another embodiment of the invention is a microsensor structure comprising a substrate having a substrate surface having an active area. A sensing electrode is on the substrate surface and has a sensing portion upon the active area. The sensing portion has an outfacing surface facing away from the substrate. A solid electrolytic medium covers the active area but does not cover the outfacing surface. The electrolytic medium, the first electrode and the gas phase form a 3-phase sensing boundary. A counter electrode is in contact with the electrolytic medium and is free from contact with the sensing electrode. A reference electrode is in contact with the electrolytic medium and is free from contact with the sensing and counter electrodes.

In accordance with an alternative embodiment of the invention a method is set forth of determining the concentration of a gaseous species. The method comprises contacting a microsensor structure with the gaseous species in a gas phase and measuring the electrochemical effect of the species between first and second electrodes. The microsensor structure comprises a substrate having an active area. The first electrode has a sensing portion on the active area. A solid electrolytic medium covers the active area. Portions of the first electrode extend outwardly beyond the electrolytic medium. The electrolytic medium, the first electrode and the gas phase form a 3-phase sensing boundary. The second electrode is in contact with the electrolytic medium and is free from contact with the first electrode.

Still another embodiment of the invention is a method of determining the concentration of a gaseous species. The method comprises contacting a microsensor structure with the gaseous species in a gas phase and measuring the electrochemical effect of the species between a sensing and a counter electrode. The microsensor structure comprises a substrate having a substrate surface having an active area. The sensing portion has an outfacing surface facing away from the substrate. A solid electrolytic medium covers the active area but does not cover the outfacing surface. The electrolytic medium, the first electrode and the gas phase form a 3-phase sensing boundary. A counter electrode is in contact with the electrolytic medium and is free from contact with the sensing electrode. A reference electrode is in contact with the electrolytic medium and is free from contact with the sensing and counter electrodes.

In accordance with still another alternative embodiment of the present invention an improved electrode structure is set forth. The improved electrode structure includes a first electrode having an outfacing surface having an uneven configuration including a plurality of outwardly extending portions. A solid electrolytic medium covers the outfacing surface with at least a substantial number of the outwardly extending portions extending outwardly beyond the electrolytic medium and not being covered thereby.

In accordance with yet another alternative embodiment of the present invention a microsensor structure is set forth comprising a substrate having a substrate surface having an active area. A first electrode is upon the substrate surface, the first electrode having a sensing portion on the active area. The sensing portion has an outfacing surface facing away from the substrate. The outfacing surface has an uneven configuration including a plurality of outwardly extending portions. A solid electrolytic medium covers the outfacing surface with the outwardly extending portions extending outwardly beyond the electrolytic medium and not being covered thereby. A second electrode is in contact with the electrolytic medium and is free from contact with the first electrode.

In accordance with another embodiment yet of the present invention an improvement is set forth in a method of determining the concentration of a particular gaseous species which comprises contacting the species with an microsensor having a substrate having a sensing electrode and a reference electrode on a surface thereof, the sensing electrode being covered by a solid electrolytic medium, and measuring the electrochemical effect of the species on the sensing electrode. The improvement comprises utilizing as the sensing electrode a first electrode having an outfacing surface having an uneven configuration including a plurality of outwardly extending portions which extend outwardly beyond the electrolytic medium and are not covered thereby.

In accordance with a still further embodiment of the present invention, a microelectrochemical sensor structure is set forth comprising a substrate having a substrate surface having an active area. A sensing electrode is in contact with the substrate surface, the sensing electrode having a sensing portion on the active area. The sensing portion has an outfacing surface facing away from the substrate surface. A solid electrolytic medium covers the outfacing surface. A plurality of conductive microparticles is dispersed in the electrolytic medium. Both a counter electrode and a reference electrode are in contact with the electrolytic medium and are free from contact with the sensing electrode and each other.

In accordance with a further embodiment of the present invention an improvement is set forth in a method of determining the concentration of a particular gaseous species which comprises contacting the species with a microelectrochemical sensor having a substrate having a sensing electrode, a counter electrode and a reference electrode on a surface thereof, the sensing electrode being covered by a solid electrolytic medium, the electrolytic medium being covered with a member permeable to the species, and measuring the electrochemical effect of the species on the sensing electrode. The improvement comprises a plurality of conductive microparticles dispersed in the electrolytic medium.

BRIEF DESCRIPTION OF DRAWINGS

The invention will be better understood by reference to the figures of the drawings wherein like numbers denote like parts throughout and wherein:

FIG. 8 is a partial section view, of an embodiment in accordance with the invention;

FIG. 9 is a partial section view of an embodiment in accordance with the invention; and FIG. 10 is a partial section view of an embodiment in accordance with the invention;

FIG. 11 is a basic sensor design in accordance with an embodiment in accordance with the invention;

FIG. 15 is a graphical representation of applied potential vs. signal-to-background current ratio;

FIG. 16 is a graphical representation of time vs. response to 500 ppm CO which illustrates response time.

BEST MODE FOR CARRYING OUT INVENTION

Figure 1:
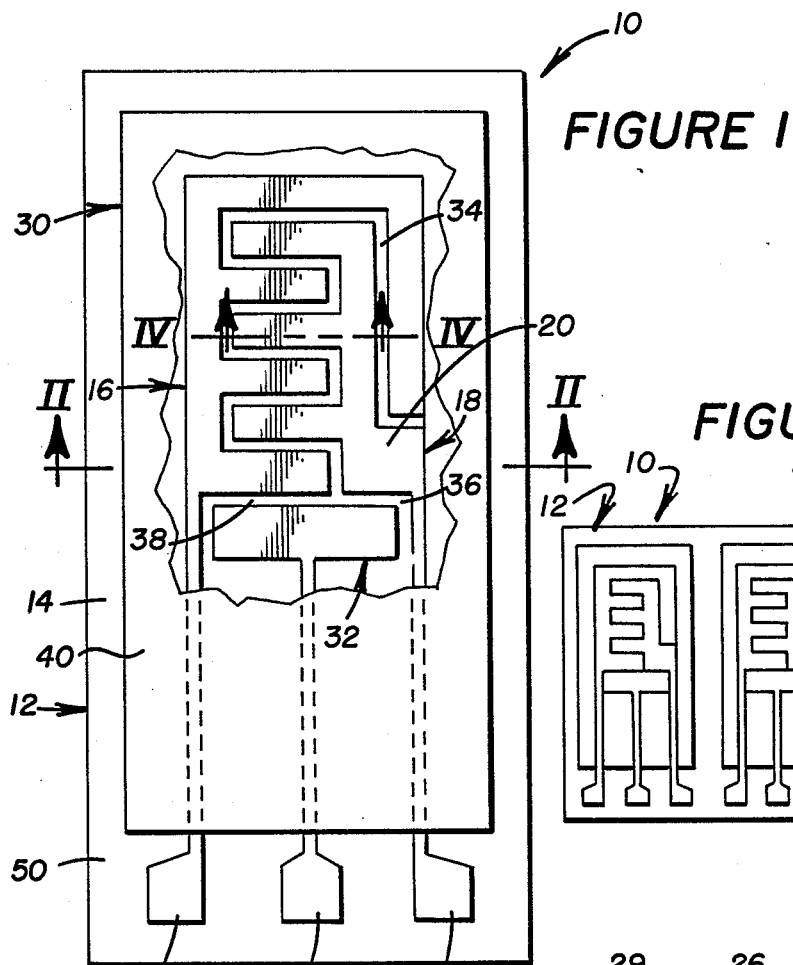
FIG. 1 illustrates, in top view, a microsensor in accordance with an embodiment of the present invention with an electrode thereon in accordance with an embodiment of the present invention.
Figure 4:
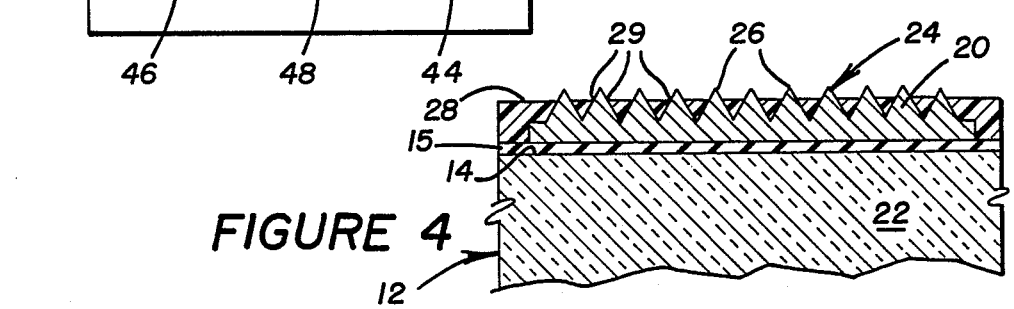
FIG. 4 is an enlarged partial cross-sectional view taken in the area IV—IV of FIG. 1.

The present invention relates to a microsensor 10 as seen in one embodiment in FIG. 1. The microsensor 10 includes a substrate 12 having a substrate surface 14 having an active area 16 upon which electrochemical reactions occur. The substrate may be made of any of a number of materials. For example, the substrate may be made of an insulative material, that is, a dielectric material, such as a non-conducting plastic or glass. Alternatively, the substrate can be made of a semiconducting material such as silicon or even of a conducting material so long as an appropriate dielectric material defines the substrate surface 14. For example, FIG. 4 shows a substrate 12 which is made of a semiconductor material, namely silicon, and wherein the substrate surface 14 is formed by IC processing techniques of a dielectric material, namely silicon dioxide. Silicon nitride or another insulative material can alternatively be used.

A first electrode 18 is on the substrate surface 14. The first electrode 18 has a sensing portion 20 on the sensing area 16 of the substrate surface 14. The sensing portion 20 has an infacing surface 22 (see FIG. 2) facing the substrate surface 14 and an outfacing surface 24 facing away from the substrate surface 14. Key to this embodiment of the present invention is the fact that the outfacing surface 24 has an uneven configuration including a plurality of outwardly extending portions 26 (FIG. 4). The outwardly extending portions 26 extend outwardly from the outfacing surface 24 preferably from about 0.01 micron to about 5 microns and may be in the nature of hills, ridges, or the like.

In accordance with the aforementioned embodiment of the present invention a solid electrolytic medium 28 covers the outfacing surface 24 of the first electrode 18 in such a manner that at least some of the outwardly extending portions 26 of the outfacing surface 24 extend outwardly beyond the electrolytic medium 28 and are not covered thereby. Thus, there is generally an extremely thin layer of the solid electrolytic medium 28 and the outwardly extending portions 26 of the outfacing surface 24 are in the nature of a plurality of small electrode material peaks exposed beyond the solid electrolytic medium 28.

The outwardly extending portions 26 of the first electrode 18, the solid electrolytic medium 28 and the surrounding gas phase form a 3-boundary sensing boundary 29 (FIG. 4). Having the outwardly extending portions 26 exposed in this manner leads to an extremely fast response time for the first electrode 18 and also to extremely high sensitivity. Generally, the solid electrolytic medium is of a thickness upon the outfacing surface of no more than about 10 microns. However, the specific extension of the solid electrolytic medium 28 is a function of the degree of extension of the outwardly extending portion 26 of the outfacing surface 24. The criticality of this embodiment lies in having the outwardly extending portions 26 extend upwardly beyond the electroyltic medium 28 to form the 3-phase sensing boundary 29.

A second (counter) electrode 30 is in contact with the electrolytic medium 28 and free from contact with the first electrode 18. In the particular embodiment illustrated the second electrode 30 is upon the substrate surface 14.

In accordance with an embodiment of the present invention a third (reference) electrode 32 may also be in contact with the electrolytic medium 28 and free from contact with the first electrode 18 and the second electrode 30. Generally, the third electrode 32 will also be in contact with the substrate surface 14.

In accordance with preferred embodiments of the present invention the first electrode 18, generally the sensing electrode, the second electrode 30, generally the counter electrode, and the third electrode 32, generally the reference electrode, as well, when present, are adjacent to one another. A first-second electrode gap 34 of generally no more than about 50 microns is advantageously present, preferably no more than about 10 microns, more preferably no more than about 5 microns and still more preferably no more than about 2 microns. Indeed, sub-micron (less than about 1 micron) gaps are particularly preferred. When there is a third electrode 32, as well, the gap 36 between the first electrode 18 and the third electrode 32 is conveniently no more than about 100 microns, although this is a far less important restrain and significantly larger gaps can be present. The size of the gap 38 between the third electrode 32 and the second electrode 30 is also of no criticality.

A dielectric wall 40 will generally be present surrounding the active area 16 and the electrolytic medium 28. A barrier 42 (FIG. 2) can be present which covers the electrolytic medium 28, the barrier 42 having openings through which an analyte gas can pass. In certain instances the barrier 42 can selectively pass a gaseous species of interest while excluding possibly interfering species. Generally, the barrier 42 will be in the nature of a polymeric material and more particularly will often be in the nature of a membrane which is gas permeable but aqueous solution impermeable. Note that the membrane need not have actual pores leading to its gas permeable nature. For example, the analyte gas may dissolve in the membrane and migrate therethrough to the electrolytic medium. In such instances, the entire microsensor 10 can be inserted in an aqueous solution and dissolved gases therein rather than form a gas phase, e.g., within the barrier 42 and can be measured. This is the case even if the electrolytic medium abuts the membrane since the analyte is in effect a gas, or gas-like, as it exits the membrane. The microsensor 10 can be utilized, for example, in vivo in blood to analyze for blood gases on a continuous basis.

Figure 3:
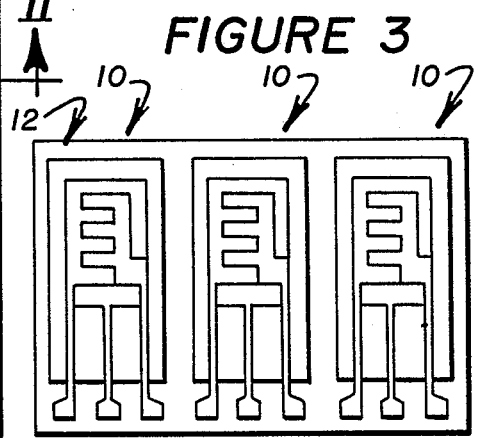
FIG. 3 is a view similar to FIG. 1 but showing an array of microsensors in accordance with the present invention on a single substrate.

FIG. 3 illustrates an embodiment of the present invention wherein a plurality of the microsensors 10 are upon the substrate surface 14 of the single substrate 12. By proper selection of the chemistries of the various electrodes 18,30,32 and of the barrier 42, for each of the sensors 10, one can provide an overall structure which is useful for analyzing for a number of different gaseous species at once, and/or can provide redundancy in measuring for one or more gaseous species.

Figure 17:
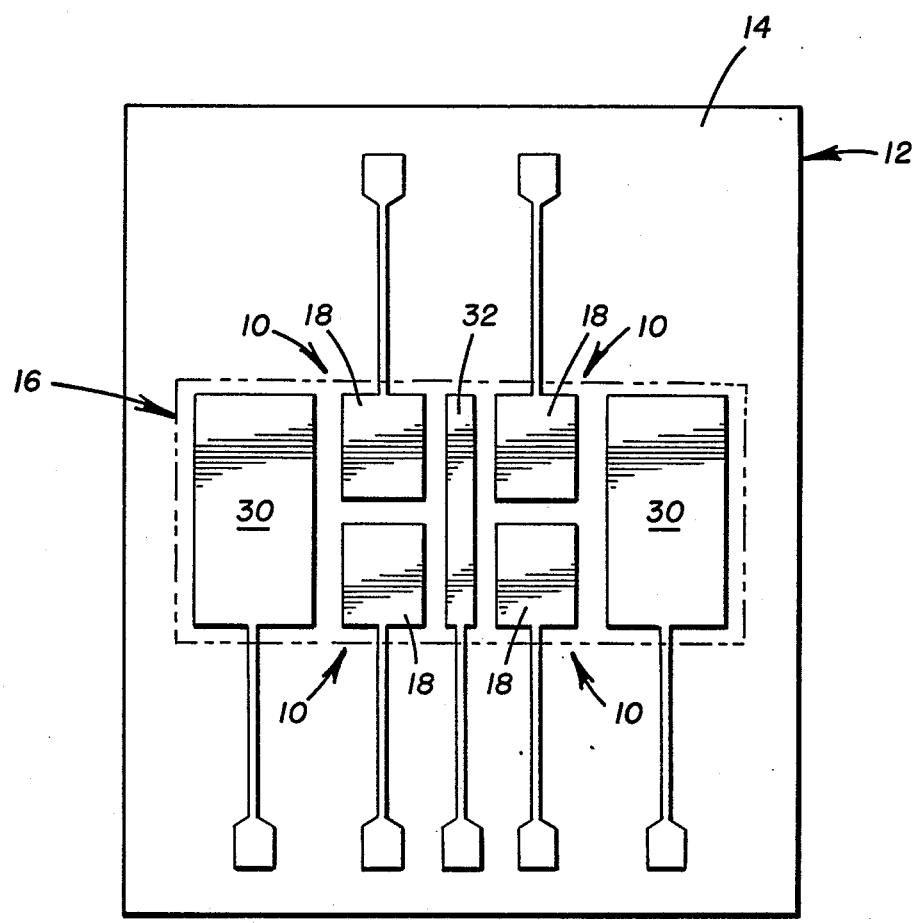
FIG. 17 shows an array of microsensors using a single reference electrode, all on a single substrate.

FIG. 17 illustrates another embodiment of the invention wherein a plurality of the microsensors 10 are upon the substrate surface 14 of the single substrate 12. In the embodiment of FIG. 17 a single reference electrode 32 is used with several different sensing electrodes 18. For example, the different sensing electrodes 18 might be made of platinum, platinum oxide, gold and iridium. The two counter electrodes 30 are positioned adjacent the sensing electrodes 18. The embodiment of FIG. 17 is more compact than, and has the same uses as, the embodiment of FIG. 3.

An aqueous reservoir 43 (FIG. 2) can be included in the substrate 12 in liquid contact with the electrolytic medium 28 to keep the electrolytic medium 28 from drying out and thereby inactivating the microsensor 10. As is seen in FIG. 10, an external aqueous reservoir 456 can alternatively, or additionally, be utilized. Such aqueous reservoirs 43,456 can be used in conjunction with all embodiments of the invention.

The first electrode 18 can be made of any of a number of materials, for example platinum, gold, silver, other platinum group metals, or other desired metals to provide detection of desired species, or electrically conductive polymers. The first electrode 18, and along with it the second electrode 30, and the third electrode 32, when present, can be formulated by vapor deposition, sputtering, or the like. Generally, such techniques as are utilized in the IC art are applicable to formulate a microsensor 10 in accordance with the present invention. This can lead to the formation of the controlled size gaps 34,36 and 38, which gaps 34,36,38 can be made quite small in size (below 5 microns and even, with care, below 1 micron). The contacts ends 44,46,48 of the electrodes 18,30 and 32, respectively, can be formulated on an appropriate contacts area 50 of the substrate 12.

Figure 5:
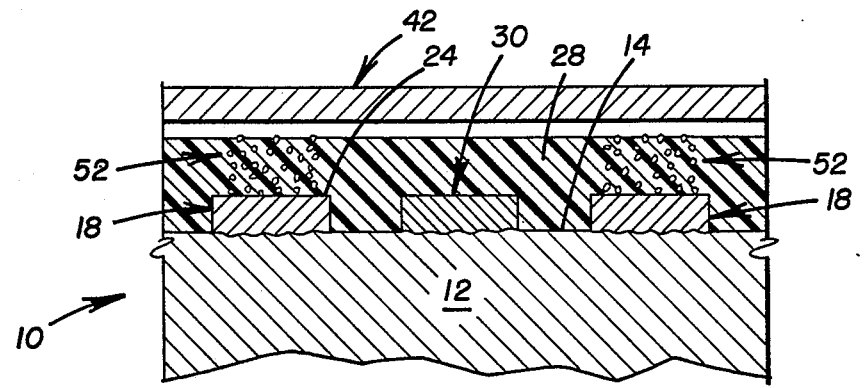
FIG. 5 is a partial section view of the sensing area of an embodiment in accordance with the invention.

FIG. 5 illustrates an embodiment of the present invention wherein the solid electrolytic medium 28 covers the entire outfacing surface 24 of the first (sensing) electrode 18. That is, in the case of the embodiment of FIG. 5 there are no outwardly extending portions 26 of the outfacing surface 24 which extend outwardly beyond the electrolytic medium 28 and are not covered thereby. However, the embodiment of FIG. 5 also gives very fast response time and high sensitivity for gas detection. This is accomplished by providing a plurality of conductive microparticles 52 dispersed in the electrolytic medium 28 and which preferably have at least portions of the uppermost thereof extending outwardly into the gas phase above the electrolytic medium 28 to form a 3-phase sensing boundary 29. Thus, the outwardly extending microparticles 52 serve as the first electrode 18 and electron conduction occurs from particle to particle down to the bulk portion 18 of the first electrode 18. For example, if the first electrode 18 is made of platinum the conductive microparticles 52 might also be of platinum, or might alternatively be of another metal. Without being bound by any theory, it should be pointed out that it is believed that with such a dispersion of conductive microparticles one obtains electron tunneling conduction through the electrolytic medium 28 whereby an analyte gas need only contact the 3-phase boundary 29 of a nearest one of the plurality of conductive microparticles in order to elicit a response from the microsensor 10. It is not essential that at least portions of the microparticles extend outwardly to form a 3-phase boundary since they may simply be close enough to the gas phase whereby diffusion to them through the electrolytic medium 28, takes only a relatively short time.

As will also be seen in FIG. 5 the substrate surface 14 may be roughened so as to provide better adhesion of the first electrode 18 thereto.

Still further in accordance with the present invention an improvement is set forth in a method of determining the concentration of a particular gaseous species which comprises contacting the species with a sensor having a substrate having a sensing electrode and a reference electrode on a surface thereof, the electrode being covered by a solid electrolytic medium, and measuring the effect of the species on the sensing electrode. The improvement comprises a plurality of conductive microparticles 52 dispersed in the electrolytic medium. The method may further include providing a counter electrode as the second electrode 30 and utilizing the counter electrode along with the sensing electrode 18, and the reference electrode 32, when measuring the effect. The various electrodes 18,30 and 32 are preferably constructed and positioned as set forth above.

Figure 6:
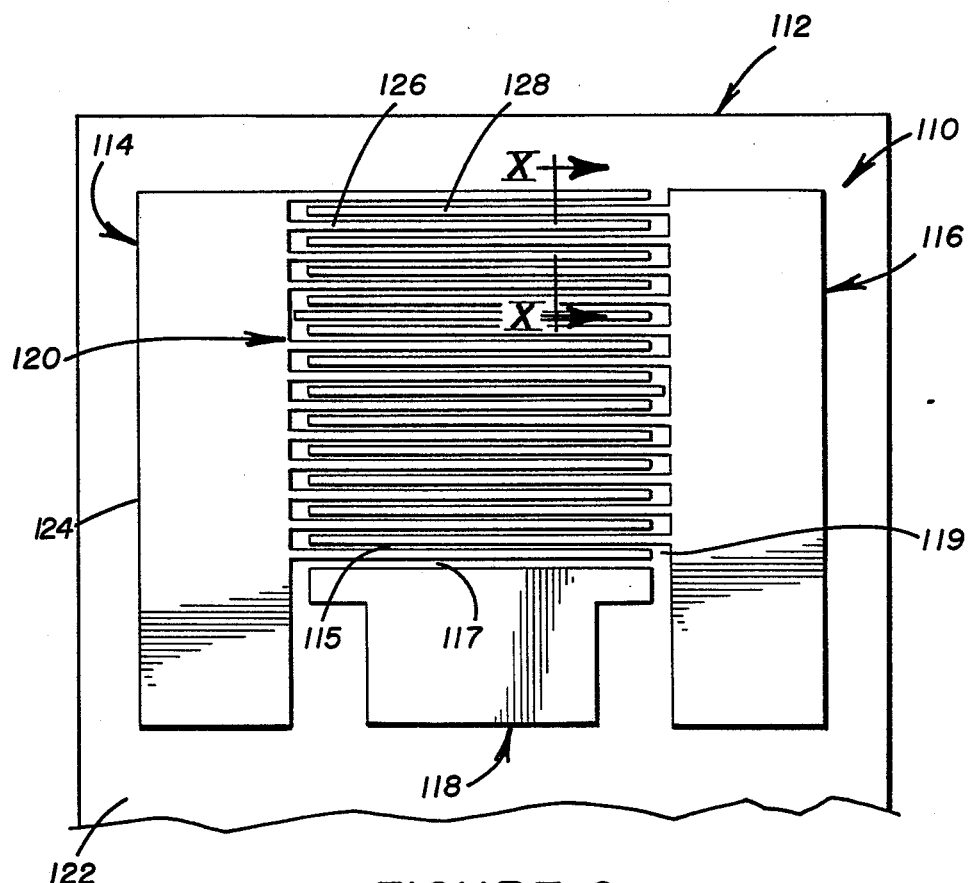
FIG. 6 is a top view of an embodiment of the present invention.
Figure 7:
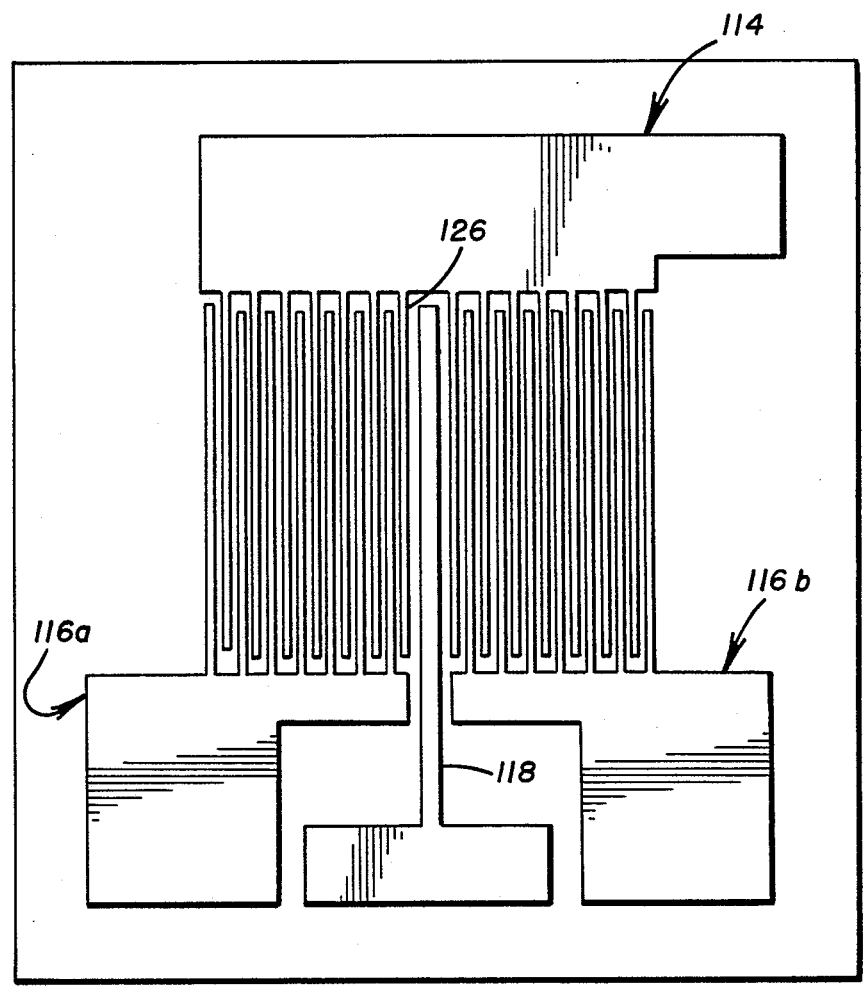
FIG. 7 is a view similar to FIG. 6 of an embodiment in accordance with the invention.

In accordance with another embodiment of the present invention an improved microsensor structure is set forth as seen in FIGS. 6 and 7. The microsensor structure 110 comprises a substrate 112 having a sensing electrode 114, a counter electrode 116 and a reference electrode 118. The electrodes define respective sensing-counter 115, sensing-reference 117 and counter-reference 119 gaps. The electrodes 114,116,118 are all mounted on an active area 120 on the surface 122 of the substrate 112. The active area 120 is covered with a solid polymer electrolyte 124 which bridges the gaps 115,117,119. The solid polymer electrolyte 124 is generally in the form of a relatively thin film. The preferred structure for this embodiment of the present invention is as illustrated, wherein the sensing electrode 114 and the counter electrode 116 are in the form of interdigited fingers 126,128 having gaps 115 generally no more than about 50 microns and, preferably no more than about 10 microns, still more preferably no more than about 5 microns and still more preferably no more than about 2 microns, with sub-micron (less than 1 micron) gaps being most preferred. The reference electrode 118 need not be interdigited with either the sensing electrode 114 or the counter electrode 116.

As is shown in FIG. 7 one may utilize two (or more) counter electrodes 116a and 116b (which are externally connected) with a single sensing electrode 114 with each of the counter electrodes 116a, 116b being interdigited with a portion of the fingers 126 of the sensing electrode 114 and with the reference electrode 118 located centrally between the two counter electrodes 116a, 116b.

Certain embodiments of the present invention are in the nature of improved microsensor structures 210,310 (FIGS. 8 and 9) for determining a gaseous species. The structures 210,310 comprise a substrate 212,312 having a surface 214,314 having an active area 216,316. A first electrode 218,318 and a second electrode 220,320 have respective sensing portions 222,322 and counter portions 224,324 on the active area 216,316. A solid electrolytic medium 226,326 covers the sensing area 216,316. The improvement in the microsensing structure 210,310 includes positioning the first electrode 218,318 sufficiently close to the second electrode 218,318 so that the time of migration of an ionic moiety, for example hydrogen ion, from one to the other of the first and second electrode 218,318 and 220,320, is no more than about 1 minute. Preferably, the time of migration of the ionic moiety is no more than about 20 seconds, more preferably no more than about 10 seconds. Also the thickness of the electrolytic medium 226,326 is restricted sufficiently so that the time of diffusion of the gaseous species through the electrolytic medium 226,326 to the sensing portion 222,322 of first electrode 218,318 is no more than about equal to the time of migration of the ionic moiety from one to the other of the first and second electrodes. In FIG. 8 this is accomplished via the first electrode 218 extending above the electrolytic medium 226 whereby diffusion time therethrough is zero. In FIG. 9 the electrolytic medium 326 extends only slightly above the first electrode 318 whereby diffusion time is short.

What is being done in the embodiments just described is to reduce (in some instances to zero) the time of diffusion of the gaseous species through the electrolytic medium sufficiently so that the limiting factor on the response time of the microsensor structure 210,310 is the rate of migration of the ionic moiety between the electrodes 218,318 and 220,320. It should be recognized that migration of analyte from the environment to the microsensor structure 210,310, or through the barrier 242,342, may in practice be slower than operation of the microsensor structure 210,310. In addition, the electrodes 218 and 318 are placed close enough together so that the time of ionic migration is very small whereby the overall time of response of the microsensor structure 210,310 is very small.

The time of diffusion through the electrolytic medium is, in accordance with certain embodiments of the present invention, reduced to zero. This occurs, for example, in the embodiments illustrated in FIGS. 2, 4 and 8. Basically, these Figures show the situation wherein the electrolytic medium 26,226,326, the first electrode, 18,218,318 and the gas phase form a 3-phase sensing boundary. Since there is no diffusion at all through the electrolytic medium, the time of such diffusion is, by definition, zero. In such an instance it is desirable to place the first and second electrodes as close together as possible since the only thing then limiting the response time of the microsensor structure is the time of diffusion of the slowest moving moiety, from one electrode to the other. It should be noted that reducing the separation of the electrodes, alone, without reducing the time of diffusion of the gaseous species through the electrolytic medium, has almost no effect since the time of diffusion of the gaseous species through the electrolytic medium is generally significantly longer than the time of migration of an ionic moiety from one electrode to the other.

Figure 2:
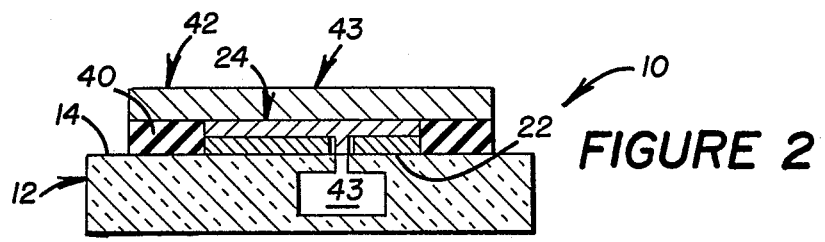
FIG. 2 is a sectional view taken along the lines II—II of FIG. 1.

In accordance with another embodiment of the present invention, as illustrated in FIGS. 2 and 10, the microsensor includes means for maintaining the solid electrolyte (which requires the presence of water to be functional) in a damp condition. The means as illustrated in FIG. 10 comprises providing an overlayer or barrier 442 which covers at least the active area 416 of the microsensor structure 410, the barrier 442 having holes 444 therethrough which communicate with the solid electrolytic medium 426 and further having one or more reservoirs 456 on the opposite side of the barrier 442 from the solid electrolytic medium 426. In this manner, water from the reservoir 456 can pass through the holes 444 and into the solid electrolytic medium 426 thereby keeping the humidity level of the solid electrolytic medium 426 at an acceptable level for extended periods of time. Note that the same barrier 442 can be over the remainder of the active area 416 thereby helping to keep down evaporation from the remainder of the solid electrolytic medium 426. Appropriate pores 444 can be provided in the barrier 442, as discussed previously with respect to the barrier 42, through which the analyte gaseous species can pass and contact the solid electrolytic medium 426 and/or the sensing electrode 418. Generally the barrier 442 would be in the nature of a membrane. The membrane can have pores which are generally such as to allow the entrance of a gaseous species but not allow the entrance of a liquid species whereby the microsensor 410 can be utilized to detect a dissolved gaseous species in a liquid by immersing the microsensor 410 beneath the surface of the liquid. Or, the analyte gas can dissolve in the barrier 442 and thereby pass therethrough. Note that in this instance the microsensor 410 is still analyzing for a gaseous species since, as discussed elsewhere, only the gaseous species reaches the solid electrolytic medium 426 and/or the sensing electrode 418.

Another method of keeping the solid electrolyte hydrated is to provide a water absorption overlayer over the solid electrolyte film. The analyte gas, for example CO and/or $CO_2$, can pass through the overlayer. The overlayer may be, for example, a hydroscopic polymer such as cellulose acetate butyrate. Or, a hydroscopic salt, for example lithium chloride and/or lithium bromide, may be incorporated in the solid polymer electrolyte film.

Specially selected solid polymer electrolyte films may be used which are themselves hydroscopic or which have a particularly high density of sulfonate groups. An example is poly(sodium 4-styrenesulfonate), $[-CH_2CH(C_6H_4SO_3Na)-]_n$. This polymer is very hydrophilic whereby signals from the sensor are made humidity independent. This particular polymer may also have its property tailored, for example by mixing with Nafion (a trademark of DuPont) polymer, so as to assure that it is not too hydrophilic or too fragile to stick to a substrate. Such techniques as are discussed above serves to make a solid polymer electrolyte film highly proton conductive or sodium conductive.

In accordance with an embodiment of the present invention the sensing electrode may be a platinum electrode. The film of the solid polymer electrolyte may be first deposited on the platinum electrode followed by a platinization process so that ultra-fine platinum particles are dispersed three-dimensionally throughout the solid polymer electrolyte layer. The platinization process is conducted prior to the pretreatment of the solid polymer electrolyte, for example the acidification and preoxidation thereof. For example, for a 50 micron gap smooth glass substrate sensor, the platinization is carried out using a galvanostatic pulse typically consisting of $-3$ k mA/cm$^2$ (cathodic) for one second and $+1.5$ mA/cm$^2$ (anodic) for 0.5 seconds in approximately 2 molar $H_2PtCl_6$ at room temperature. The right value of the current density must be chosen (depending on the gap size, the degree of surface roughness and the specific resistance and thickness of the solid polymer electrolyte) to avoid bridging (short-circuiting) sensing and counter electrodes; for example. If the thickness of the solid polymer electrolyte film is approximately 1 micron, about 3 to 4 hours (a total of about 1.1 to 1.9 coulombs) is required to deposit an adequate amount of platinum.

Any of a number of different types of electrolytic media 28 can be utilized. For example, the electrolytic medium 28 can be a solution, e.g., a water based solution. Alternatively, the electrolytic medium 28 can be a hydrogel. Preferable, however, particularly for voltammetric measurements, are solid electrolytes, including solid polymeric electrolytes such as Nafion (a trademark of DuPont) which is part of a class of solid polymeric ion exchangers which conduct ions upon exposure to water. Probably the best known examples are membranes made from polystyrene with fixed negative sites (sulfonate, carboxylate or phosphonate) or fixed positive sites (quaternary ammonium or quaternary phosphonium). Selection as far as ions are concerned with these materials is almost exclusively on the basis of charge and for ions with the same charge discrimination is very slight. For voltammetric sensing the use of these materials is new. Other examples of solid polymeric electrolytes besides Nafion (which is a perfluorinated ionomer) are sulfonated styrene-divinyl benzene resins and divinyl napthalene sulfonic acid polymer.

Such polymers are characterized chemically and physically in that they have a hydrophobic nature with ionic (hydrophilic) clusters inside. They conduct ions upon hydration. They exclude co-ions up to the Donnan failure point at which stage ions of both types can penetrate into the resin. Neutral molecules can diffuse readily through such membranes and especially large organic molecules can dissolve within the more hydrophobic resins.

Resins can also be used as reference solutions (see, for example, French patent publication No. 2,158,905). These ion exchange resins have been used as the electrolytic medium for a potentiometric $CO_2$ sensor (see, for example, U.S. Pat. No. 3,730,868).

Useful gels for incorporation within the sensor structure include, without limitation: methylcellulose, polyvinyl alcohol, agar, carboxycellulose, gelatin, agarose, deionized gelatin, polyacrylamide, polyvinyl pyrrolidone, polyhydroxyethylacrylate, poly-2-hydroxyethyl methacrylate, and polyacrylic acid. They are characterized in that they constitute thickened (more viscous) solutions. They are hydrophilic in natural and include synthetic polymeric film forming materials.

The electrolytic medium can alternatively be selected from a family of inorganic oxide solid proton conductors, e.g., hydrogen uranyl phosphate, protonated $\beta''$-alumina, zirconium phosphates or antimonic acids.

Means (e.g., the barrier 42) is usually provided for encapsulating the electrolytic medium 28 and the sensing electrode 18. In the embodiments illustrated the barrier 42 can be any convenient polymer. It is generally preferred that the encapsulation material be such as to be impermeable to water vapor so that the water content of the solid electrolyte remains relatively constant whereby the properties of the gas sensor remain relatively constant with time. The barrier 42 may be, for example, in the nature of a membrane. The barrier 42 provides entry into the microsensor 10 of a selected moiety in response to contact of a selected species with its outfacing surface 43. Either the selected species will pass through the barrier 42 and will then constitute the selected moiety, or contact of the selected species with the barrier 42 will lead to the introduction of a different moiety into the microsensor 10. The barrier 42 is generally at least substantially impermeable to the electrolytic medium 28 to prevent escape and/or mixing with any analyte solution exterior of the barrier 42.

The barrier 42 may encapsulate the entire microsensor 10. Alternatively, the barrier 42 may only cover the sensing area 16, or part or all of the substrate surface 14. It may be desirable to encapsulate the remainder of the microsensor 10, or even all of the microsensor 10 including the barrier 42, as a protection against contamination. Generally, an inert encapsulating layer (not shown) will serve the purpose. The encapsulating layer, when present, must provide access (via, for example, pores or holes therethrough) to the barrier 42. It can be formulated as can the barrier 42.

A number of materials may serve as the barrier 42. For example, the barrier 42 can comprise a gas permeable liquid impermeable membrane. This is useful in the situation wherein the sensor is used in a liquid to detect dissolved gases, for example, if the microsensor 10 is utilized in blood.

Other types of materials for utilizing as the barrier 42 are teflon membranes, silicone rubber membranes, silicon polycarbonate rubber membranes, mylar, nylon 6, polyvinyl alcohol, polyvinyl chloride, methylcellulose, cellulose acetate, high density polyethylene, polystyrene, natural rubber, fluorosilicone, dimethylsilicon rubber, any appropriately perforate photoresist polymer, and dimethylsilicon. It is generally preferred that the membranes utilized be solution castable so as to make fabrication of the membrane more easily accomplished.

The barrier 42 can be constructed by, for example solution casting, separate casting on a different substrate and physical transfer, heat shrinking in place, solution casting utilizing an ink-jet printer, spin coating, or dip coating. If the barrier 42 is in the nature of uniform latex microspheres, made for example of polystyrene, styrene-butydiene, or Teflon (trademark of DuPont), such microspheres can be placed in position utilizing an ink-jet like technique, by dipping, by solvent spraying, or the like. If the barrier 42 is of the nature of or includes activated carbon or similar materials it can be placed in position by ink-jet type printing, solvent casting, or the like. If the barrier includes, for example, permanganate coated alumina or other substance which serves to remove nitric oxide, it can be placed in position similarly to the carbon particles.

Various types of sensing electrodes 18 can be used. These include, for example, electrodes 18 of platinum, platinum black, silver, gold, iridium, palladium, palladium/silver, iridum dioxide, platinum black/paladium, platinum oxide, and mixtures thereof, electronically conductive polymers, and generally any of the electrodes normally utilized in electrochemical measurements. A sensing electrode 18 will generally be chosen which is responsive to a particular gaseous species. Various conventional materials can be utilized as the counter electrode 30 and as the reference electrode 32. Table 1 sets forth, as examples only, a short list of gases, and electrochemical systems which have been used to determine them.

Also in accordance with the present invention an improvement is set forth in a method of determining the concentration of a particular gaseous species which comprises contacting the species with a sensor having a substrate having a sensing electrode and a reference electrode on a surface thereof, the electrode being covered by a solid electrolytic medium, and measuring the electrochemical effect of the species on the sensing electrode. The improvement comprises utilizing as the sensing electrode a first electrode 18 as described in any of the embodiments above. The method may further include providing a counter electrode as the second electrode 30, all as set forth above, and utilizing the counter electrode 30 along with the sensing electrode 18 and the reference electrode 32 when measuring the electrochemical effect. The various electrodes 18, 30 and 32 are preferably constructed and positioned as set forth above.

extending portion 26 are desired on a sensing electrode 18.

While the substrate surface 14 is illustrated as being planar it should be recognized that the invention is not limited to such a structure. Thus, the first electrode 18 usually generally conforms with the substrate surface 14, whatever its shape, planar, spherical, or the like.

The electrochemical analysis which can be made in

TABLE 1

| Gas | Electrocatalyst | Electrolyte | Potential | Sensitivity (Detection Limit*) |
|---|---|---|---|---|
| CO | Platinum-catalyzed Teflon-bonded diffusion electrode | 3.4 M $H_2SO_4$ | 1.2 V vs. NHE | 10 $\mu$A/ppm (0.2 ppm) |
| CO | Platinoid black catalyst with Teflon binder | Hydrated solid polymer (Nafion) | 1.15 V vs. NHE | 2.2 $\mu$A/ppm (0.9 ppm) |
| (CO) | Gold-catalyzed Teflon-bonded diffusion electrode | 4 M $H_2SO_4$ | (1.4 V vs. NHE) | (0.03 $\mu$A/ppm) |
| NO | Gold catalyzed Teflon-bonded | 4 M $H_2SO_4$ | >1.2 V vs. NHE | 7 $\mu$A/ppm (0.3 ppm) |
| NO | Graphite with Teflon binder | Hydrated solid polymer (Nafion) | 1.25 V vs. NHE | 2.6 $\mu$A/ppm (0.8 ppm) |
| $NO_2$ | Graphite with Teflon binder | Hydrated solid polymer (Nafion) | 0.75 V vs. NHE | −2.9 $\mu$A/ppm (0.7 ppm) |
| $NO_2$ | Gold-catalyzed Teflon-bonded diffusion electrode | 4 M $H_2SO_4$ | <1.0 V vs. NHE | −8 $\mu$A/ppm (0.25 ppm) |
| $H_2S$ | Gold-catalyzed Teflon-bonded diffusion electrode | 28% $H_2SO_4$ | 1.45 V vs. NHE | 46 $\mu$A/ppm (40 ppb) |
| $N_2H_4$ | Gold-catalyzed Teflon-bonded diffusion electrode | 23% KOH | 1.1 V vs. NHE | 40 $\mu$A/ppm (50 ppb) |
| $CH_4$ | Teflon-bonded platinum black electrode | 2 M $NaClO_4$ in $\gamma$-butyrolactane | 0.8 V vs. Ag/AgCl | 1 $\mu$A % $CH_4$ (3000 ppm) |
| $O_2$ | Gold (cathode) | Alkaline | −0.6 to −1.0 V vs. Ag/$Ag_2$O anode** | 0.05 $\mu$A/% $O_2$ (0–100% $O_2$) |
| $O_2$ | Ultrathin electrode (gold?) | Alkaline | Lead anode** | 2.5–3 nA/ppm $O_2$ (0.1 ppm to 100% $O_2$) |
| $H_2$ | Platinum black powder | Antimonic acid | Platinum black counter electrode** | 50 $\mu$A/% $H_2$ (400 ppm) |

*Detection limit (minimum detectable quantity) is calculated as the value yielding a signal-to-noise ratio of 2, using a typical noise level 1 $\mu$A of amperometric gas sensors.
**Quasi-amperometric (polargraphic), no reference.
NHE = normal hydrogen electrode.

The microsensors 10,110,210,310 and, 410 in accordance with the invention can be constructed, generally, following the techniques of the IC industry. For example, the metals can be deposited by sputtering or evaporation, electron-beam or ohmic evaporation onto a resist masked substrate 12 or by a lift-off technique. These techniques are particularly useful for providing closely placed sensing electrodes 18 and counter electrodes 30, such as the fingers 126,128 as shown in FIGS. 7 and 8 with very small gaps 115. Solid polymer electrolytes, when used, can be provided by using lift off technology or ink-jet printer like technology. Hydrogels, when used, can be provided as are solid polymer electrolytes. The thickness of the electrolytic medium 28 is controlled by Sensing electrodes 18 with outwardly extending portions 26 can be formed by any of several techniques. For example, the electrode 18 can be fabricated as discussed above followed by a platinization, gold deposition, etc., process, as appropriate, generally similarly to the technique described elsewhere herein for dispersing ultrafine platinum particles three-dimensionally through a solid polymer electrolyte. The solid polymer electrolyte (or other electrolytic medium 28) is only deposited after the platinization, etc., is carried out if outwardly accordance with the methods of and/or using the sensors of the present invention includes voltammetric, potentiometric, coloumbic, conductometric and AC analysis.

In accordance with the present invention the microsensors of the invention can be used for differential pulse voltammetry (DPV) methods. In such a technique potential is scanned and the resultant current response is differentiated, thereby generating more information from a single sensor. The use of the DPV technique to achieve required selectivity is a direct application of the characteristic thermodynamic potentials of the gases being analyzed. Note that certain gases of interest, for example CO, $H_2$, $C_2H_5OH$, NO, and $NO_2$, have characteristic thermodynamic potentials of, respectively, −103, 0, 87, 957 and 1093 mV vs NHE. In practice, however, each reaction requires an additional potential called overpotential, the amount of which depends on electrocatalyst, in order to proceed at a measurable rate.

This technique is useful if the gas to be sensed exists in a mixture containing several reactive components that exhibit close thermodynamic potential (e.g., CO, $H_2$ and $C_2H_5OH$). If one considers a simple example wherein a mixture of gas A and gas B exists, gas A and gas B will exhibit current vs potential curves with different limiting currents $I_A$ and $I_B$. By differentiating the current versus potential curves one obtains two sharp, clearly separated peaks with characteristic potentials, $E_A$ and $B_B$. The peak current values are proportional to the gas concentrations. Thus the DPV technique can provide the potential-control led selectivity for a microsensor through precise measurements of the peak values. These are closely related to the thermodynamic potentials of the gases and are characteristics of each gaseous species.

In addition, the nature of this technique allows the microelectrochemical sensor to rezero the background several times each second, thereby limiting any background drift. Also, this technique improves the sensitivity because the DPV current readout eliminates most of the capacitive charging current and provides an especially good signal to noise ratio.

The invention will be better understood by reference to the following experimental sections.

INSTRUMENTATION AND EXPERIMENTAL PROCEDURE

The experimental setup included a microprocessor-controlled gas-handling system (Tylan Co.). Premixed gas mixtures, 200 ppm CO in air, 100 ppm $NO_2$ in air, 100 ppm NO in $N_2$, 1000 ppm ethanol in $N_2$ (primary standard grade, manufactured by Union Carbide Company Linde Division, South San Francisco, Calif., and distributed by Almac Cryogenic, Inc.), were used to evaluate the microelectronic gas sensors, and hydrocarbon-free air was used as a blank (background) gas. The sample gas (200 ppm CO) and the blank gas (air or $N_2$) were introduced to a stainless-steel gas-sensor chamber at a nominal flow rate of 150 $cm^3$/min using flowmeters. The sensor potential is controlled by a PAR Model 173 potentiostat equipped with a PAR Model 175 Universal Programmer. For low current (less than 1 $\mu A$) measurements, an in-vivo voltammograph (Bioanalytical Systems, Inc. Model CV 37) is used. A (Hewlett-Packard Model 7644A) X-Y-t recorder records signals as a function of time.

Humidified gas samples were prepared as needed by passing dry gas samples through a humidifier prior to entering the gas chamber. The humidifier comprises three Gore-Tex (Type A, 3 mm ID, pore size 2 $\mu m$, porosity 50 percent) porous Teflon tubes with three different lengths, approximately 1, 2 and 3 cm, which are equilibrated with water vapor pressure at room temperature, and provide approximate humidity values of 10 to 15, 20 to 25 and 35 to 40 percent relative humidity (RH), respectively. The relative humidity of the gas mixture was determined by placing a humidity sensor (General Eastern Instruments Corp. Model 800B humidity and temperature indicator) in the gas line right after the gas chamber.

EXAMPLE

The responses to CO and various other gases were studied using a planar type microelectrode. The basic sensor design is shown in FIG. 11. The masks are designed to produce gaps that range in size from 5 to 50 microns between adjacent microelectrodes. A smooth $Al_2O_3$ ceramic (Kyocera type A 493) was used as the substrate. Platinum was used as electrode material for all electrodes. A chromium adhesion layer of approximately 5 nm was deposited first, followed by approximately 200 to 280 nm of platinum, sputtered in a vacuum of $2 \times 10^{-6}$ torr in a mrc rf sputtering system with the substrate being water cooled. The metallized substrate was then coated with about 3 $\mu m$ of EM Industries' negative polyimide photoresist and photolithographically patterned. The polyimide was prebaked at 65° C. for 15 minutes and postbaked at 140° C. for 60 minutes. The unwanted portions of the platinum film was etched away by $Ar^+$ sputtering-etching techniques. The remaining photoresist was then removed by an oxygen plasma etching process. A 1 micron thick Nafion film, which was used as the electrolyte, prepared by solution casting 17.5 $\mu l$ of diluted (1:5 ethanol) stock solution (stock Nafion solution, 5% by weight, Solution Technology, Inc.) into a 5 mm $\times$ 7 mm window (made by 3M type 470 tape). The film was dried at room temperature from about 2 hours. The Nafion film was then acidified in a beaker containing 20% $H_2SO_4$ at approximately 60° C. for about 3 hours.

Figure 12:
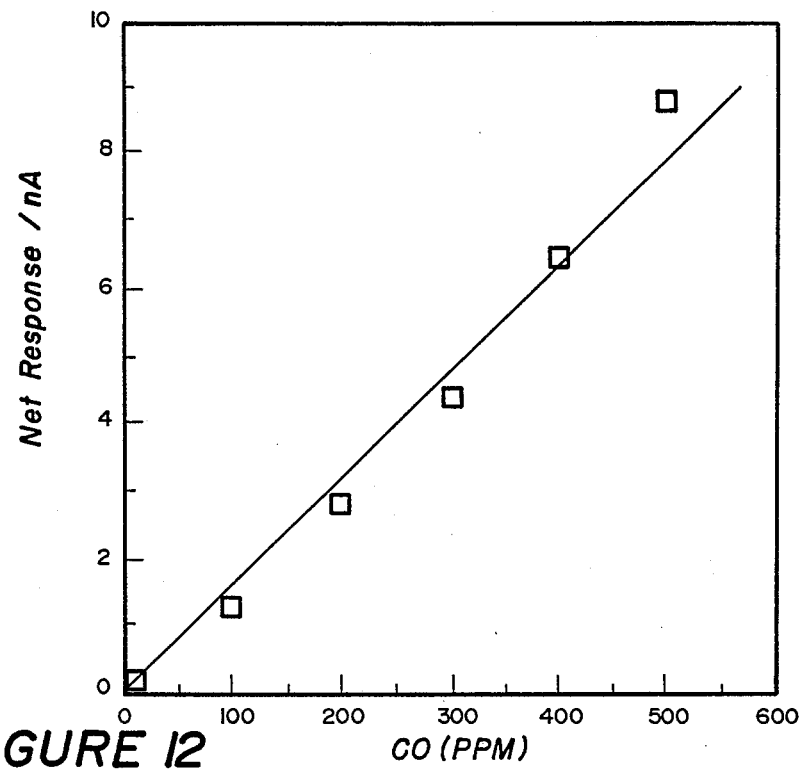
FIG. 12 is a graphical representation of CO concentration vs. net response.
Figure 13:
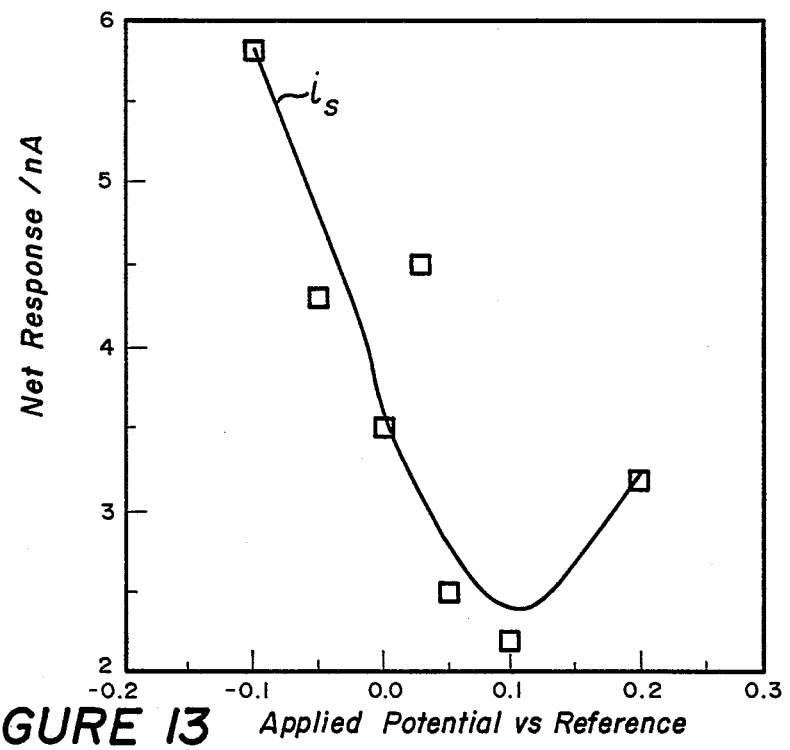
FIG. 13 is a graphical representation of applied potential vs. net response for 500 ppm CO.
Figure 14:
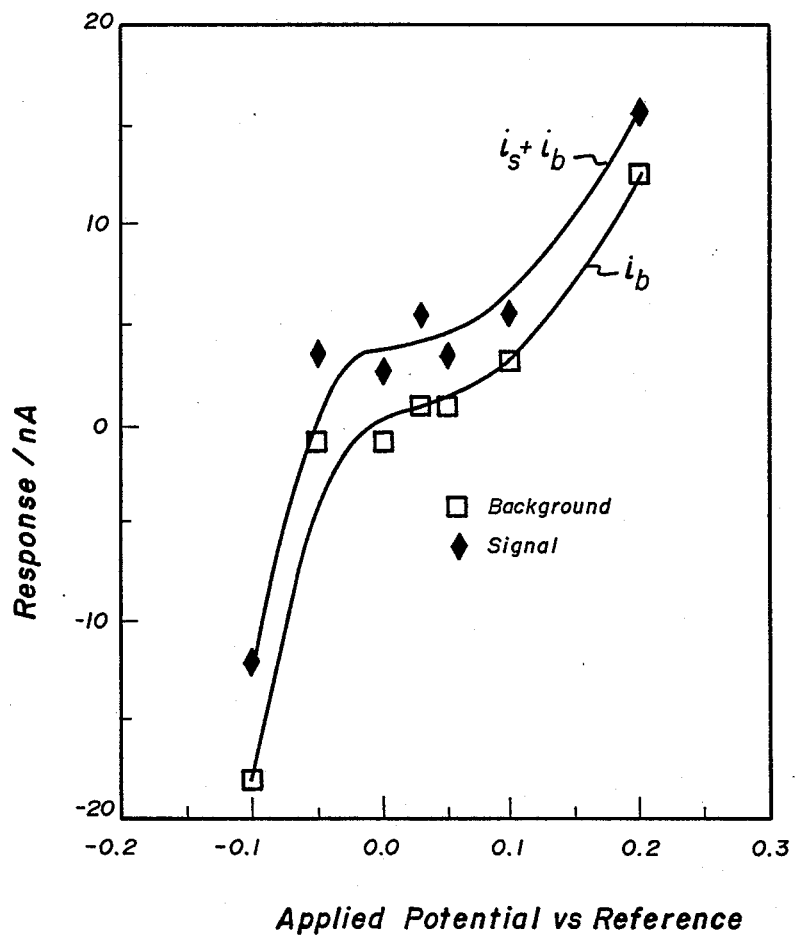
FIG. 14 is a graphical representation of applied potential vs. background current and response for 500 ppm CO.

FIG. 12 indicates steady-state signals ($i_s$) as function of CO concentration at an applied potential of $-50$ mv. The sensor was tested in the CO concentration range of 100 to 500 ppm on a planar type platinum sensor with a 10 micron gap between adjacent electrodes. A reasonable linearity is seen. FIGS. 13, 14 and 15 illustrate the net response ($i_s$), background current ($i_b$), and total signal ($i_s + i_b$), and the values of the signal to background current ratio ($i_s/i_b$), as a function of the applied potential (sensing electrode potential vs. the built-in platinum reference electrode) at 45% RH (relative humidity), respectively. The net response is defined as the difference in the measured currents when the sensor is exposed to air (background current) and to 500 ppm CO. FIG. 16 shows the current responses to CO as a function of time at an applied potential of $-0.05$ V (the response time to 500 ppm CO in air is about 1 minute).

The sensor responses to other gases such as ethanol (800 ppm in air), $H_2$ (800 ppm in air), NO (80 ppm in air), and $NO_2$ (100 ppm in air) were also studied. Tables 2, 3, 4 and 5 show the current response to 500 ppm CO, 800 ppm ethanol, 80 ppm NO, and 100 ppm $NO_2$, respectively, as a function of the applied potential. In the range of $-0.1$ to $+0.2$ volts, $-0.05$ V is the most ideal potential for CO sensing because the CO response was very stable and the response time very fast. The response to ethanol vapor was unstable and non-reproducible. The sensor response to $H_2$ in the same potential range was also measured, and unstable current response occurred throughout the range. For a practical CO sensor development, for example, it is clear that the pre-selected applied potential the CO sensor exhibited good response to CO and to a large extent can exclude interfering gases.

TABLE 2

| Applied Potential | i(b) nA | i(s) nA | i(s)/(b) | Rt(s) |
| --- | --- | --- | --- | --- |
| −0.1 | −17.9 | 5.8 | 0.34 | 60 |
| −0.05 | −0.8 | 4.3 | 5.4 | 58 |
| 0.0 | −0.9 | 3.5 | 3.9 | 60 |
| +0.03 | 1.0 | 4.5 | 4.5 | 60 |
| +0.05 | .97 | 2.5 | 2.6 | 90 |
| +0.1 | 3.3 | 2.2 | 0.67 | 60 |
| +0.2 | 12.5 | 3.2 | 0.26 | 40 |

Current Response to 500 ppm CO as a function of Applied Potential
RH = 45%

TABLE 3

| Applied Potential | i(b) nA | i(s) nA | i(s)/(b) | Rt(s) |
|---|---|---|---|---|
| −0.1 | −19.8 | 138 | 7.0 | 60 |
| −0.05 | −27 | 195 | 7.2 | 40 |
| 0.0 | −0.3 | 75 | 250 | 65 |
| +0.03 | 0.9 | 100 | 111 | 120 |
| +0.05 | 1.0 | 180 | 106 | 168 |
| +0.1 | 4.0 | 232.5 | 58.1 | 180 |
| +0.2 | 13.0 | 212.5 | 16.3 | 80 |

Current Response to 800 ppm EtOH as a function of Applied Potential
RH = 45%

TABLE 4

| Applied Potential | i(b) nA | i(s) nA | i(s)/(b) | Rt(s) |
|---|---|---|---|---|
| −0.1 | — | — | — | — |
| −0.05 | −21.0 | −18.0 | 0.86 | 180 |
| 0.0 | 0.7 | −3.7 | 5.3 | 180 |
| +0.03 | 3.9 | 7.4 | 1.9 | 220 |
| +0.05 | 5.5 | 17.6 | 3.2 | 320 |
| +0.1 | 7.4 | 30.0 | 4.1 | 300 |
| +0.2 | 4.9 | 100.0 | 20.0 | 60 |

Current Response to 80 ppm NO as a function of Applied Potential
RH = 45%

TABLE 5

| Applied Potential | i(b) nA | i(s) nA | i(s)/(b) | Rt(s) |
|---|---|---|---|---|
| −0.1 | — | — | — | — |
| −0.05 | −2.1 | −7.7 | 3.7 | 40 |
| 0.0 | −1.0 | 9.5 | 5.5 | 60 |
| +0.03 | 5.2 | −26.0 | 5.0 | 220 |
| +0.05 | 8.0 | 56.0 | 7.0 | 145 |
| +0.1 | 29.0 | 136.0 | 4.7 | 230 |
| +0.2 | — | — | — | — |

Current Response to 100 ppm $NO_2$ as a function of Applied Potential
RH = 45%

INDUSTRIAL APPLICABILITY

The present invention provides a novel electrode structure 18, a novel microsensor 10, and an improved method of determining the concentration of gaseous species. All of the above is useful in analyzing for any one gaseous species among other gaseous species, or, in accordance with certain embodiments, with gaseous species which are dissolved in a fluid, for example a body fluid such as blood. Extremely fast response time is provided along with extremely high sensitivity. Uses include the following: portable environmental gas analyzers, detection of hazardous gases, fire alarms, gas leak detectors, monitoring and controlling chemical processes, alarm badges for safety inspectors, monitoring and regulating exhaust gases from engines, oil furnaces or industrial burners, control of indoor air quality, and gas chromatography detector, among others. And, construction is relatively inexpensive utilizing standard IC techniques.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

We claim:
1. A voltammetric microsensor structure, comprising:
a substrate having an active area on a surface thereof;
a sensing electrode having a portion thereof on said active area;
a counter electrode having a portion thereof on said active area;
a reference electrode having a portion thereof on said active area;
said sensing electrode, said counter electrode and said reference electrode defining respectively therebetween a sensing-counter gap, a sensing-reference gap and a counter-reference gap;
a solid polymer electrolyte bridging said gaps;
a barrier covering said solid polymer electrolyte electrolyric medium, said barrier being permeable to an analyte gas; and
an aqueous reservoir internal of said substrate in flow contact with said electrolyte.
2. A microsensor structure as set forth in claim 1, wherein said barrier is water impermeable.
3. A microsensor structure as set forth in claim 1, further including:
a dielectric wall extending outwardly from said substrate surface about said active area and said solid polymer electrolyte.
4. A microsensor structure as set forth in claim 1, wherein said substrate is of a dielectric material.
5. A microsensor structure as set forth in claim 1, wherein said substrate is of a semiconductor material and further including:
an insulator between said substrate and said electrodes.
6. A microsensor as set forth in claim 1, wherein said sensing-counter electrode gap is no more than about 50 microns.
7. A microsensor structure as set forth in claim 1, wherein said barrier is water impermeable.
8. A microsensor structure as set forth in claim 1, further including:
a plurality of sets of said sensing, counter and reference electrodes, each of said sets being on said substrate, each of said sets being in contact with a respective one of a corresponding plurality of solid polymer electrolytes, said polymer electrolytes being electrically isolated from one another.
9. A method of voltammetrically determining the concentration of a gaseous species, comprising:
contacting a microsensor structure with the gaseous species in a gas phase and voltammetrically measuring the electrochemical effect of the species between sensing and counter electrode, the microsensor structure comprising a substrate having a sensing electrode, a counter electrode and a reference electrode, the electrodes defining respective sensing-counter, sensing-reference and counter-reference gaps between portions thereof mounted on an active area on the surface of the substrate, the gaps being bridged by a solid polymer electrolyte, a barrier covering said electrolyte, said barrier being permeable to an analyte gas and an aqueous reservoir internal of said substrate in flow contact with said electrolyte.
10. A method as set forth in claim 9, further including:
positioning said sensing and counter electrodes sufficiently closely adjacent one another whereby said sensing-counter electrode gap is no more than about 50 microns.

11. A method as set forth in claim 10, wherein said solid polymer electrolyte is of a thickness upon said sensing electrode of no more than about 10 microns.

12. In a microsensor structure comprising a substrate having a surface having an active area, first and second adjacent electrodes having, respectively, sensing and counter portions on the active area; and an electrolytic medium covering the active area, the improvement comprising:
  positioning the first and second electrodes sufficiently close together on said active area so that the time of migration of an ionic moiety from one to the other of the electrodes is no more than about 1 minute;
  restricting the thickness of the electrolytic medium to be no more than about 10 microns so that the time of diffusion of the gaseous species through the electrolytic medium to the first electrode is no more than about equal to the time of migration of the ionic moiety from one to the other of the electrodes;
  a barrier covering said electrolytic medium, said barrier being permeable to an analyte gas; and
  an aqueous reservoir internal of said substrate in flow communication with said electrolytic medium.

13. In a microsensor structure comprising a substrate having a surface having an active area, first and second adjacent electrodes having, respectively, sensing and counter portions on the active area; and an electrolytic medium covering the active area, the improvement comprising:
  positioning the first and second electrodes sufficiently close together on said active area so that the time of migration of an ionic moiety from one to the other of the electrodes is no more than about 1 minute;
  restricting the thickness of the electrolytic medium to be no more than about 10 microns so that the time of diffusion of the gaseous species through the electrolytic medium to the first electrode is no more than about equal to the time of migration of the ionic moiety from one to the other of the electrodes;
  a barrier covering said electrolytic medium, said barrier being permeable to an analyte gas;
  a third electrode having a reference portion in contact with said electrolytic medium and free from contact with said first and second electrodes; and
  an aqueous reservoir internal of said substrate in flow contact with said electrolytic medium.

14. A microsensor structure for sensing an analyte in a gas phase, comprising:
  a substrate having a surface having an active area;
  a sensing electrode having a sensing portion on said active area, said sensing portion comprising a plurality of sensing fingers and having an outfacing surface facing away from said substrate;
  a counter electrode having a counter portion on said active area, said counter portion comprising a plurality of counter fingers, said counter fingers being positioned between and aligned generally along said sensing fingers to define sensing finger-counter finger gaps of no more than about 50 microns;
  a reference electrode having a reference portion on said active area and being free from contact with said sensing and counter electrodes;
  an electrolytic medium on said active area bridging said sensing finger-counter finger gaps and communicating said reference portion with said sensing portion, said electrolytic medium covering the active area by not covering the outfacing surface of said sensing electrode, the electrolytic medium, the sensing electrode and the gas phase forming a 3-phase sensing boundary;
  a barrier covering said electrolytic medium, said barrier being permeable to an analyte gas; and
  an aqueous reservoir internal of said substrate in flow contact with said electrolytic medium.

15. A microsensor structure for sensing an analyte in a gas phase, comprising:
  a substrate having a substrate surface having an active area;
  a sensing electrode on the substrate surface having a sensing portion upon the active area, the sensing portion having an outfacing surface facing away from the substrate;
  a solid electrolytic medium covering the active area but not covering the outfacing surface, the electrolytic medium, the first electrode and the gas phase forming a 3-phase sensing boundary;
  a counter electrode in contact with the electrolytic medium and free from contact with the sensing electrode; and
  a reference electrode in contact with the electrolytic medium and free from contact with the sensing and counter electrodes;
  a barrier covering said electrolytic medium, said barrier being permeable to an analyte gas; and
  an aqueous reservoir internal of said substrate in flow contact with said electrolytic medium.

16. A microsensor structure as set forth in claim 15, wherein said barrier is water impermeable.

17. A microsensor structure as set forth in claim 15, further including:
  a dielectric wall extending outwardly from said substrate surface about said active area and said electrolytic medium.

18. A microsensor structure as set forth in claim 15, wherein said substrate is of a dielectric material.

19. A microsensor structure as set forth in claim 15, wherein said substrate is of a semiconductor material and further including:
  an insulator between said substrate and said first and second electrodes.

20. A microsensor as set forth in claim 15, wherein said sensing and counter electrodes are adjacent one another and are separated by a sensing-counter electrode gap of no more than about 50 microns.

21. A microsensor as set forth in claim 20, further including:
  a barrier covering said electrolytic medium, said barrier being permeable to an analyte gas.

22. A microsensor as set forth in claim 21, wherein said member is water impermeable.

23. A microsensor as set forth in claim 20, wherein said solid electrolytic medium is of a thickness upon said outfacing surface of no more than about 10 microns.

24. A microsensor as set forth in claim 23, further including:
  a barrier covering said electrolytic medium, said barrier being permeable to an analyte gas.

25. A microsensor structure as set forth in claim 15, further including:

a plurality of sets of said sensing and counter electrodes, each of said sets being on said substrate, said sets each being in contact with a respective one of a corresponding plurality of solid electrolytic mediums, said electrolytic mediums being electrically isolated from one another.

26. An electrode structure, comprising:
a first electrode having a sensing portion having an outfacing surface having uneven configuration including a plurality of outwardly extending portions; and
an electrolytic medium covering said outfacing surface with said outwardly extending portions extending outwardly beyond said electrolytic medium and not being covered thereby.

27. An electrode structure as set forth in claim 26, wherein said outfacing extending portions extend outwardly from said outfacing surface from about 0.01 micron to about 5 microns.

28. An electrode structure as set forth in claim 27, wherein said electrolytic medium is of a thickness upon said outfacing surface of no more than about 10 microns.

29. A microsensor structure, comprising:
a substrate having a substrate having an active area;
a first electrode on with said substrate surface, said first electrode having a sensing portion on said active area, said sensing portion having an infacing surface facing said substrate surface and an outfacing surface facing away from said substrate surface, said outfacing surface having an uneven configuration including a plurality of outwardly extending portions;
an electrolytic medium covering said outfacing surface with said outwardly extending portions extending outwardly beyond said electrolytic medium and not being covered thereby; and
a second electrode on said electrolytic medium and free from contact with said first electrode.

30. A microsensor as set forth in claim 29, further including:
a barrier covering said electrolytic medium, said barrier being permeable to an analyte gas.

31. A microsensor structure as set forth in claim 30, wherein said barrier is water impermeable.

32. A microsensor as set forth in claim 30, further including:
an aqueous reservoir in flow contact with said electrolytic medium.

33. A microsensor structure as set forth in claim 29, further including:
a dielectric wall extending outwardly from said substrate surface about said active area and said electrolytic medium.

34. A microsensor structure as set forth in claim 29, wherein said substrate is of a dielectric material.

35. A microsensor structure as set forth in claim 29, wherein said substrate is of a semiconductor material and further including:
an insulator between said substrate and said first and second electrodes.

36. A microsensor as set forth in claim 29, wherein said outfacing extending portions extend outwardly from said outfacing surface from about 0.01 micron to about 5 microns.

37. A microsensor as set forth in claim 29, wherein said second electrode is on said substrate surface and wherein said first and second electrodes are adjacent one another and are separated by a first-second electrode gap of no more than about 50 microns.

38. A microsensor as set forth in claim 37, further including:
a barrier covering said electrolytic medium, said barrier being permeable to an analyte gas.

39. A microsensor as set forth in claim 38, wherein said member is water impermeable.

40. A microsensor as set forth in claim 29, further including:
a third electrode in contact with said electrolytic medium and free from contact with said first and second electrodes.

41. A microsensor as set forth in claim 40, wherein said first electrode is a sensing electrode, said second electrode is a counter electrode and said third electrode is a reference electrode.

42. A microsensor as set forth in claim 41, wherein said second and third electrodes are on said substrate surface, wherein said first and second electrodes are adjacent one another and are separated by a first-second electrode gap of no more than about 50 microns.

43. A microsensor structure as set forth in claim 29, wherein said outwardly extending portions extend upwardly from said outfacing surface from about 0.01 micron to about 5 microns.

44. A microsensor as set forth in claim 43, wherein said solid electrolytic medium is of a thickness upon said outfacing surface of no more than about 10 microns.

45. A microsensor as set forth in claim 44, further including:
a barrier covering said electrolytic medium, said barrier being permeable to an analyte gas.

46. A microsensor structure as set forth in claim 45, further including:
an aqueous reservoir in flow contact with said electrolytic medium.

47. A microsensor structure as set forth in claim 46, wherein said outfacing extending portions extend outwardly from said outfacing surface from about 0.01 micron to about 5 microns.

48. A microsensor structure as set forth in claim 47, wherein said second electrode is on said substrate surface and wherein said first and second electrodes are adjacent one another and are separated by first-second electrode gap of no more than about 50 microns.

49. A microsensor as set forth in claim 47, further including:
a third electrode in contact with said electrolytic medium and free from contact with said first and second electrodes.

50. A microsensor structure as set forth in claim 49, wherein said first electrode is a sensing electrode, said second electrode is a counter electrode and said third electrode is a reference electrode.

51. A microsensor structure as set forth in claim 50, wherein said second and third electrodes are on said substrate surface, wherein said first and second electrodes are adjacent one another and are separated by first-second electrode gap of no more than about 50 microns.

52. A microsensor structure as set forth in claim 51, further including:
an aqueous reservoir in flow contact with said electrolytic medium.

53. A microsensor structure as set forth in claim 51, wherein said member is water impermeable.

54. A microsensor structure as set forth in claim 29, further including:
a plurality of said first electrodes and a plurality of said second electrodes, each of said first electrodes being on said substrate, said first electrodes each being in contact with a respective one of a corresponding plurality of solid electrolytic mediums, said electrolytic mediums being electrically isolated from one another.

55. In a method of determining the concentration of a particular gaseous species which comprises contacting the species with a sensor having a substrate having a sensing electrode and a counter electrode on a surface thereof, the electrodes being covered by an electrolytic medium, and measuring the electrochemical effect of said species on said sensing electrode, the improvement comprising:
utilizing as said sensing electrode a first electrode having an outfacing surface having an uneven configuration including a plurality of outwardly extending portions which extend outwardly beyond said electrolytic medium and are not covered thereby.

56. A method as set forth in claim 55, wherein said method further includes:
providing a reference electrode as a third electrode on said surface and utilizing said reference electrode along with said sensing and counter electrode when measuring said effect.

57. A method as set forth in claim 56, wherein said outfacing extending portions extend outwardly from said outfacing surface from about 0.01 micron to about 5 microns.

58. A method as set forth in claim 55, further including:
positioning said sensing and counter electrodes adjacent one another and separated by sensing-counter electrode gap of no more than about 50 microns.

59. A method as set forth in claim 58, wherein said solid electrolytic medium is of a thickness upon said outfacing surface of no more than about 10 microns.

60. A method as set forth in claim 59, wherein said solid electrolytic medium comprises a solid polymer electrolyte.

61. A method as set forth in claim 55, wherein said outwardly extending portions extend outwardly from said outfacing surface from about 0.01 micron to about 5 microns.

62. A microsensor structure, comprising:
a substrate having a substrate surface having an active area;
a first electrode in contact with said substrate surface, said first electrode having a sensing portion on said active area, said sensing portion having infacing surface facing said substrate surface and an outfacing surface facing away from said substrate surface;
a solid electrolytic medium covering said outfacing surface, said solid electrolytic medium having a plurality of conductive microparticles dispersed therein; and
a second electrode in contact with said electrolytic medium and free from contact with said first electrode.

63. A microsensor as set forth in claim 62, further including:
a barrier covering said electrolytic medium, said barrier being permeable to an analyte gas.

64. A microsensor as set forth in claim 63, wherein said barrier is water impermeable.

65. A microsensor as set forth in claim 63, further including:
an aqueous reservoir in flow contact with said electrolytic medium.

66. A microsensor structure as set forth in claim 62, wherein said substrate is of a dielectric material.

67. A microsensor structure as set forth in claim 62, wherein said substrate is of a semiconductor material and further including:
an insulator between said substrate and said first and second electrodes.

68. A microsensor as set forth in claim 62, wherein said second electrode is on said substrate surface and wherein said first and second electrodes are adjacent one another and are separated by a first-second electrode gap of no more than about 50 microns.

69. A microsensor as set forth in claim 68, further including:
a barrier covering said electrolytic medium, said barrier being permeable to an analyte gas.

70. A microsensor as set forth in claim 69, wherein said member is water impermeable.

71. A microsensor as set forth in claim 62, further including:
a third electrode in contact with said electrolytic medium and free from contact with said first and second electrodes.

72. A microsensor as set forth in claim 71, wherein said first electrode is a sensing electrode, said second electrode is a counter electrode and said third electrode is a reference electrode.

73. A microsensor as set forth in claim 72, wherein said second and third electrodes are on said substrate surface and wherein said first and second electrodes are adjacent one another and are separated by a first-second electrode gap of no more than about 50 microns.

74. A microsensor as set forth in claim 62, wherein said solid electrolytic medium is of a thickness upon said outfacing surface of no more than about 10 microns.

75. A microsensor as set forth in claim 74, further including:
a barrier covering said electrolytic medium, said barrier being permeable to an analyte gas.

76. A microsensor structure as set forth in claim 75, further including:
an aqueous reservoir in flow contact with said electrolytic medium.

77. A microsensor structure as set forth in claim 76, wherein said second electrode is on said substrate surface and wherein said first and second electrodes are adjacent one another and are separated by first-second electrode gap of no more than about 50 microns.

78. A microsensor as set forth in claim 77, further including:
a third electrode in contact with said electrolytic medium and free from contact with said first and second electrodes.

79. A microsensor structure as set forth in claim 78, wherein said first electrode is a sensing electrode, said second electrode is a counter electrode and said third electrode is a reference electrode.

80. A microsensor structure as set forth in claim 79, wherein said second and third electrodes are on said substrate surface, wherein said first and second electrodes are adjacent one another and are separated by first-second electrode gap of no more than about 50 microns.

81. A microsensor structure as set forth in claim 80, further including:
an aqueous reservoir in flow contact with said electrolytic medium.

82. A microsensor structure as set forth in claim 80, wherein said member is water impermeable.

83. A microsensor structure as set forth in claim 62, further including:
a plurality of sets of said first and second electrodes, each of said sets being on said substrate, said sets each being in contact with a respective one of a corresponding plurality of solid electrolytic mediums, said electrolytic mediums being electrically isolated from one another.

84. In a method of determining the concentration of a particular gaseous species which comprises contacting the species with a sensor having a substrate having a sensing electrode and a counter electrode on a surface thereof, the electrode being covered by a solid electrolytic medium, and measuring the effect of said species on the sensing electrode, the improvement comprising:
including a plurality of conductive microparticles dispersed in said solid electrolytic medium.

85. A method as set forth in claim 84, wherein said method further includes:
providing a reference electrode as a third electrode on said surface and utilizing said reference electrode along with said sensing and counter electrode when measuring said effect.

86. A method as set forth in claim 85, further including:
positioning said sensing and counter electrodes adjacent one another and separated by sensing-counter electrode gap of no more than about 50 microns.

87. A method as set forth in claim 84, wherein said solid electrolytic medium is of a thickness upon said outfacing surface of no more than about 10 microns.

88. A method as set forth in claim 87, wherein said solid electrolytic medium comprises a solid polymer electrolyte.

* * * * *